United States Patent
Fogarty et al.

(10) Patent No.: US 6,291,243 B1
(45) Date of Patent: Sep. 18, 2001

(54) P ELEMENT DERIVED VECTOR AND METHODS FOR ITS USE

(75) Inventors: Patrick Fogarty, Santa Cruz; Joseph Lipsick, Stanford, both of CA (US)

(73) Assignees: The Board of Trustees of the Leland Stanford Jr. University, Palo Alto; Tosk, Inc., Santa Cruz, both of CA (US)

( * ) Notice: Subject to any disclaimer, the term of this patent is extended or adjusted under 35 U.S.C. 154(b) by 0 days.

(21) Appl. No.: 09/561,176

(22) Filed: Apr. 27, 2000

Related U.S. Application Data

(60) Provisional application No. 60/131,406, filed on Apr. 28, 1999.

(51) Int. Cl.[7] .................................................. C12N 15/63
(52) U.S. Cl. ...................... 435/455; 435/320.1; 435/325; 435/468; 435/410; 536/23.1; 536/23.2
(58) Field of Search .............................. 800/25; 435/462, 435/196, 69.1, 464, 325, 194, 193, 320.1; 536/24.1, 23.2, 23.1; 530/350

(56) References Cited

U.S. PATENT DOCUMENTS

| | | |
|---|---|---|
| 4,670,388 | 6/1987 | Rubin et al. |
| 5,719,055 | 2/1998 | Cooper . |

OTHER PUBLICATIONS

Beall et al, Drosophila P element transposase is a novel site–specific endonuclease, Genes and Development, vol. 11, 2137–2151 (1997).*

Ivics et al. (1996). "Identification of functional domains and evolution of Tc1–like transportable elements" *Proc. Natl. Acad. Sci.*, vol. 93: 5008–5013.

Ivics et al. (1997). "Molecular Reconstruction of *Sleeping Beauty*, a Tc1–like Transposon from Fish, and its Transposition in Human Cells" Cell, vol. 91: 501–510.

Luo et al. (1998). "Chromosomal transposition of a Tc1/mariner–like element in mouse embryonic stem cells" *Proc. Natl. Acad. Sci.*, vol. 95: 10769–10773.

Rio et al. (1986). "Identification and Immunochemical Analysis of Biologically Active Drosophila P Element Transposase" Cell, Vol. 44: 21–32.

Rio et al. (1988). "Evidence for Drosophila P Element Transposase Activity in Mammalian Cells and Yeast" *J. Mol. Biol.*, vol. 200: 411–415.

Schouten et al. (1998). "Transposon Tc1 of the nematode Caenorhabditis elegans jumps in human cells" Nucleic Acid Research, vol. 26(12): 3013–3017.

Rio, D.C. "Regulation of Drosophilia P element transposition", Trends in Genetics, Sep. 1991, vol. 7, No. 9, pp. 282–287.

* cited by examiner

*Primary Examiner*—Sean McGarry
*Assistant Examiner*—Konstantina Katcheves
(74) *Attorney, Agent, or Firm*—Bret E. Field; Bozicevic, Field & Francis

(57) ABSTRACT

Novel P element derived vectors and methods for their use to insert an exogenous nucleic acid into the genome of a target cell are provided. The subject vectors have a pair of P element transposase recognized insertion sites, e.g. 31 base pair inverted repeats, flanking at least two transcriptionally active genes. In practicing the subject methods, a vector of the subject invention is introduced into the target cell under conditions sufficient for transposition to occur. The subject methods find use in a variety of applications in which the insertion of an exogenous nucleic acid into the genome of a target cell is desired, e.g. include research, synthesis and therapeutic applications.

24 Claims, 2 Drawing Sheets

P ELEMENT DERIVED VECTOR AND METHODS FOR ITS USE

CROSS REFERENCE TO RELATED APPLICATIONS

Pursuant to 35 U.S.C. §119 (e), this application claims priority to the filing date of the United States Provisional Patent Application Ser. No. 60/131,406 filed Apr. 28, 1999; the disclosure of which are herein incorporated by reference.

INTRODUCTION

1. Field of the Invention

The field of this invention is nucleic acid vectors.

2. Background of the Invention

The introduction of an exogenous nucleic acid sequence (e.g. DNA) into a cell, a process known as "transformation," plays a major role in a variety of biotechnology and related applications, including research, synthetic and therapeutic applications. Research applications in which transformation plays a critical role include the production of transgenic cells and animals. Synthetic applications in which transformation plays a critical role include the production of peptides and proteins. Therapeutic applications in which transformation plays a key role include gene therapy applications. Because of the prevalent role transformation plays in the above and other applications, a variety of different transformation protocols have been developed.

In many transformation applications, it is desirable to introduce the exogenous DNA in a manner such that it is incorporated into a target cell's genome. One means of providing for genome integration is to employ a vector that is capable of homologous recombination. Techniques that rely on homologous recombination can be disadvantageous in that the necessary homologies may not always exist; the recombination events may be slow, etc. As such, homologous recombination based protocols are not entirely satisfactory.

Accordingly, alternative viral based transformation protocols have been developed, in which a viral vector is employed to introduce exogenous DNA into a cell and then subsequently integrate the introduced DNA into the target cell's genome. Viral based vectors finding use include retroviral vectors, e.g. Maloney murine leukemia viral based vectors. Other viral based vectors that find use include adenovirus derived vectors, HSV derived vectors, sindbis derived vectors, etc. While viral vectors provide for a number of advantages, their use is not optimal in many situations. Disadvantages associated with viral based vectors including immunogenicity, viral based complications, and the like.

Accordingly, there is continued interest in the development of additional vectors for use in transformation protocols. Of particular interest is the development of non-viral vectors that provide for stable integration of exogenous DNA in a cell genome through a mechanism other than homologous recombination.

Relevant Literature

U.S. Patents of interest include: U.S. Pat. Nos. 5,719,055 and 4,670,388. Other references of interest include: Rio et al., "Identification and Immunochemical Analysis of Biologically Active Drosophila P Element Transposase," Cell (Jan. 17, 1986) 44:21–32; and Rio et al., "Evidence for Drosophila P Element Transposase Activity in Mammalian Cells and Yeast," J. Mol. Biol. (1988) 200: 411–415.

Additional articles of interest include: Schouten et al., Nuc. Acids Res. (1998) 26:3013–3017; Ivics et al., Cell (1997) 91: 501–510; Luo et al., Proc. Nat'l Acad. Sci USA (1998) 95:10769–10773; and Ivics et al., Proc. Nat'l Acad. Sci. USA (1996) 93:5008–5013.

SUMMARY OF THE INVENTION

P element derived vectors and methods for their use in the insertion of an exogenous nucleic acid into a target cell genome are provided. The vectors of the subject invention include a pair of P element transposase recognized insertion sequences, e.g. P element derived 31 base pair inverted repeats, flanking at least two transcriptionally active genes. In practicing the subject methods, a vector as described above carrying an exogenous nucleic acid is introduced into a target cell under conditions sufficient for transposition of the exogenous nucleic acid from the vector into the target cell genome. The subject methods find use in a variety of transformation applications, including research, polypeptide synthesis and therapeutic applications.

DESCRIPTION OF THE SPECIFIC EMBODIMENTS

Figure 1:
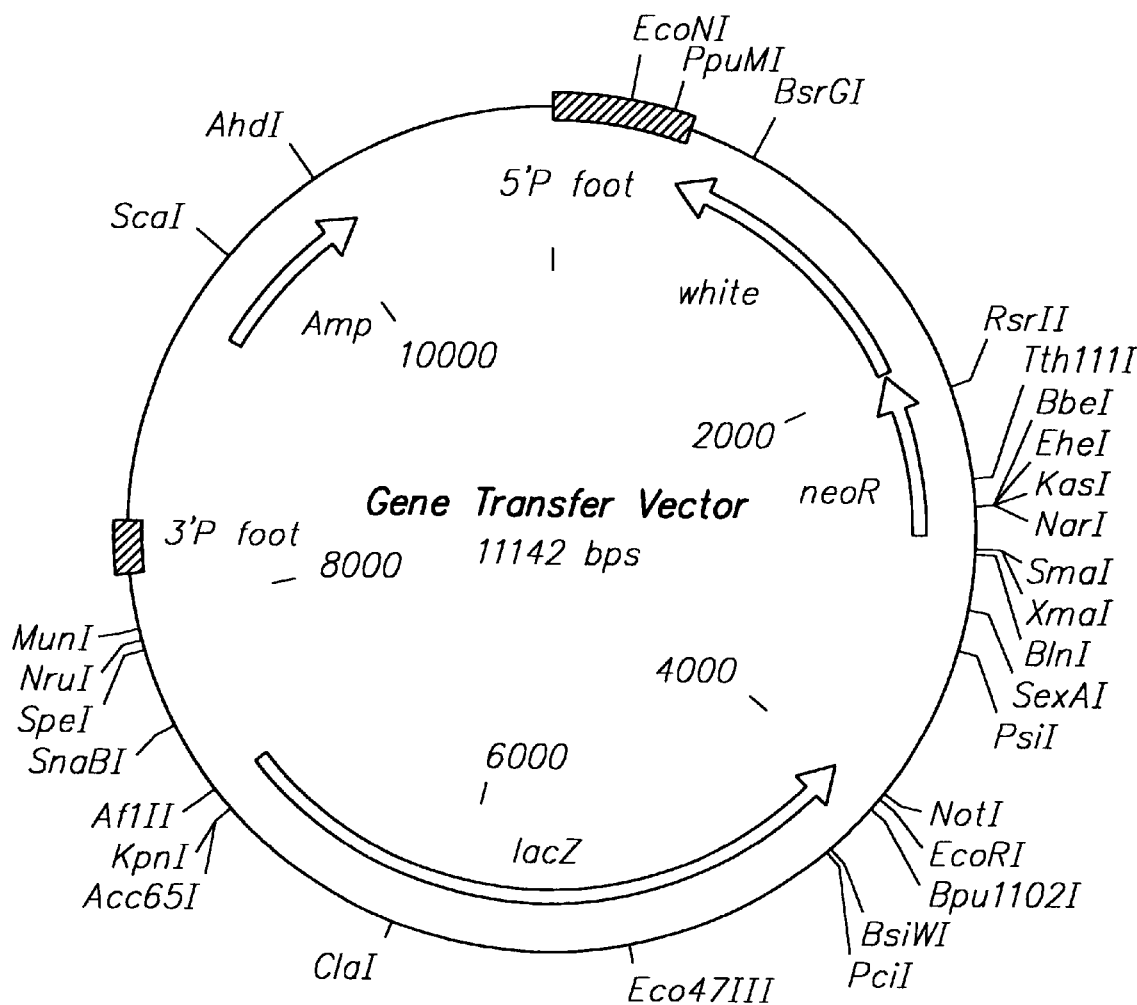
FIG. 1 is a diagram of a vector according to the subject invention.

P element derived vectors and methods for their use in the insertion of an exogenous nucleic acid into the genome of a cell are provided. The subject vectors include two P element transposase recognized insertion sequences, e.g. P element derived 31 base pair inverted repeats, flanking at least two transcriptionally active genes. In the subject methods, a vector according to the invention that includes an exogenous nucleic acid is introduced into a target cell under conditions sufficient for insertion of the exogenous nucleic acid into the target cell genome to occur. The subject methods find use in a variety of different applications, including gene therapy applications. In further describing the subject invention, the subject vectors will be described first, followed by a discussion of the methods of using the subject vectors for transformation of a target cell.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

Vectors

The vectors of the subject invention are P element derived vectors, i.e. P element derived transposon vectors, by which is meant that the vectors include at least the P element transposase recognized insertion sequences of the Drosophila P element. As such, the subject vectors include a pair of the 31 base pair inverted repeat domain of the P element, or the functional equivalent thereof, i.e. a domain recognized by the P element encoded transposase. The 31 base pair inverted repeat (i.e. P foot) is disclosed in Beall et al., "Drosophila P-element transposase is a novel site-specific endonuclease," Genes Dev (Aug. 15, 1997)11(16):2137–51.

In the subject vectors, the pair of P element encoded transposase recognized insertion sequences (i.e. P feet) flank at least two transcriptionally active genes. By at least two is meant two or more, usually no more than five, and more usually no more than four, where the number of transcriptionally active genes in the vector is often two or three. In certain embodiments, the exogenous nucleic acid that is inserted into a target cell genome in the subject methods, described in greater detail infra, is one of the transcriptionally active genes of the vectors. By transcriptionally active gene is meant a coding sequence that is capable of being expressed under intracellular conditions, e.g. a coding sequence in combination with any requisite expression regulatory elements that are required for expression in the intracellular environment of the target cell with which the subject vector is to be employed. As such, the transcriptionally active genes of the subject vectors typically include a stretch of nucleotides or domain, i.e. expression module, that includes a coding sequence of nucleotides in operational combination, i.e. operably linked, with requisite trascriptional mediation or regulatory element(s). Requisite transcriptional mediation elements that may be present in the expression module include promoters, enhancers, termination and polyadenylation signal elements, splicing signal elements, and the like.

Preferably, the expression module includes transcription regulatory elements that provide for expression of the gene in a broad host range. A variety of such combinations are known, where specific transcription regulatory elements include: SV40 elements, as described in Dijkema et al., EMBO J. (1985) 4:761; transcription regulatory elements derived from the LTR of the Rous sarcoma virus, as described in Gorman et al., Proc. Nat'l Acad. Sci USA (1982) 79:6777; transcription regulatory elements derived from the LTR of human cytomegalovirus (CMV), as described in Boshart et al., Cell (1985) 41:521; hsp70 promoters, (Levy-Holtzman, R. and I. Schechter (Biochim. Biophys. Acta (1995) 1263: 96-98) Presnail, J. K. and M. A. Hoy, (Exp. Appl. Acarol. (1994) 18: 301–308)) and the like.

In many embodiments, at least one of the transcriptionally active genes or expression modules present in the subject vectors is a selectable marker. A variety of different genes have been employed as selectable markers, and the particular gene employed in the subject vectors as a selectable marker is chosen primarily as a matter of convenience. Known selectable marker genes include: the thimydine kinase gene, the dihydrofolate reductase gene, the xanthine-guanine phosporibosyl transferase gene, CAD, the adenosine deaminase gene, the asparagine synthetase gene, the antibiotic resistance genes, e.g. tet$^r$, amp$^r$, Cm$^r$ or cat, kan$^r$ or neo$^r$ (aminoglycoside phosphotransferase genes), the hygromycin B phosphotransferase gene, and the like.

In addition, the subject vectors typically include at least one restriction endonuclease recognized site, e.g. restriction site, located between the P feet which serves as a site for insertion of an exogenous nucleic acid. A variety of restriction sites are known in the art and may be included into the vector, where such sites include those recognized by the following restriction enzymes: HindIII, PstI, SalI, AccI, HincII, XbaI, BamHI, SmaI, XmaI, KpnI, SacI, EcoRI, and the like. In many embodiments, the vector includes a polylinker, i.e. a closely arranged series or array of sites recognized by a plurality of different restriction enzymes, such as those listed above.

The inter P feet domain of the vectors, i.e. that domain or region of the vector located or positioned between the P feet which includes the at least two transcriptionally active genes and the exogenous nucleic acid, when present, may vary greatly in size. Typically, the size of this inter P feet domain (i.e. P feet flanked domain) is at least about 50 bp in length, usually at least about 1000 bp in length and more usually at least about 2000 bp in length, where the length of this domain may be as long as 150,000 bp or longer, but generally does not exceed about 20,000 bp in length and more usually does not exceed about 10,000 bp in length.

In certain embodiments, the subject vectors further include a transposase encoding domain, i.e. a region of nucleotides having a sequence that encodes a protein having transposase activity, particularly a transposase activity that recognizes the P feet of the P element, specifically a protein having the P element transposase activity, i.e. P element transposase or a functional equivalent or mimetic thereof. The amino acid sequence of the P element transposase is disclosed in Rio et al., Cell (Jan. 17, 1986) 44: 21–32. A specific transposase encoding nucleic acid that may be present on the subject vectors is that found in pTURBO, where the sequence of this plasmid is disclosed in W. R. Engels, Bioess. 14: 681–686 (1992). When present on the subject vectors, this P element transposase encoding region or domain is located outside the region flanked by the P feet. In other words, the transposase encoding region is located external to the region flanked by the P feet, i.e. outside the inter P-feet domain described supra. Put another way, the tranposase encoding region is positioned to the left of the left terminal P foot or the right of the right terminal P foot.

The subject vectors can be used to stably insert a wide variety of endogenous and/or exogenous nucleic acids into the genome of a target cell (exogenous means a nucleic acid having a sequence that is not present in the target cell while endogenous means a nucleic acid that pre-exists in the target cell, prior to insertion). The nature of the nucleic acid will vary depending the particular protocol being performed. For example, in research applications, the exogenous or endogenous nucleic acid may be a novel gene whose protein product is not well characterized. In such applications, the vector is employed to stably introduce the gene into the target cell and observe changes in the cell phenotype in order to characterize the gene. Alternatively, in protein synthesis application, the exogenous or endogenous nucleic acid encodes a protein of interest which is to be produced by the cell. In yet other embodiments where the vector is employed as a gene therapy vector, the exogenous or endogenous nucleic acid is a gene having therapeutic activity, i.e. a gene that encodes a product of therapeutic utility. The nucleic acid may vary greatly in size. Generally, the size of the nucleic acid that is carried by the vector is at least about 50 bp, usually at least about 1000 bp and more usually at least about 2000 bp, where the length may be as long as 150,000 bp or longer, but generally does not exceed about 20,000 bp and usually does not exceed about 10,000 bp. In many embodiments, the exogenous nucleic acid is long, by which is meant that it ranges in length from about 30 to 50 kb.

The subject vectors may further comprise one or more elements required for amplification of the vector in a prokaryotic host, e.g. *E. coli*. Elements that may be included on the vector for use in amplification of the vector in a prokaryotic host include: an origin of replication, a selectable marker, and the like.

A representative vector of the subject invention is depicted in FIG. 1.

In addition to the above described vectors that include at least two transcriptionally active genes, also provided are vectors that include a single transciptionally active gene. In vectors of this embodiment of the subject invention, the promoter that is part of the transcriptionally active gene may be any of those described above, e.g. SV40, with the proviso that the promoter is not a CMV promoter. Vectors of this embodiment that include a single transcriptionally active gene may be prepared and used as described below, where the following description is provided in terms of vectors that include at least two transcriptionally active genes.

Methods of Preparing the Subject Vectors

The vectors of the subject invention may be produced by standard methods of restriction enzyme cleavage, ligation and molecular cloning. One protocol for constructing the subject vectors includes the following steps. First, purified nucleic acid fragments containing desired component nucleotide sequences as well as extraneous sequences are cleaved with restriction endonucleases from initial sources, e.g the Drosophila P element. Fragments containing the desired nucleotide sequences are then separated from unwanted fragments of different size using conventional separation methods, e.g., by agarose gel electrophoresis. The desired fragments are excised from the gel and ligated together in the appropriate configuration so that a circular nucleic acid or plasmid containing the desired sequences, e.g. sequences corresponding to the various elements of the subject vectors, as described above is produced. Where desired, the circular molecules so constructed are then amplified in a prokaryotic host, e.g. *E. coli*. The procedures of cleavage, plasmid construction, cell transformation and plasmid production involved in these steps are well known to one skilled in the art and the enzymes required for restriction and ligation are available commercially. (See, for example, R. Wu, Ed., Methods in Enzymology, Vol. 68, Academic Press, N.Y. (1979); T. Maniatis, E. F. Fritsch and J. Sambrook, Molecular Cloning: A Laboratory Manual, Cold Spring Harbor Laboratory Press, Cold Spring Harbor, N.Y. (1982); Catalog 1982–83, New England Biolabs, Inc.; Catalog 1982–83, Bethesda Research Laboratories, Inc. An example of how to construct a vector of the present invention is provided in the Experimental section, infra, and depicted in FIG. 2.

Methods of Using the Subject Vectors

The subject vectors find use in a variety of applications in which it is desired to introduce and stably integrate an exogenous or endogenous nucleic acid into the genome of a target cell. As mentioned above, exogenous nucleic acid means a stretch of nucleotides that is not initially present in the target cell, while endogenous nucleic acid means a nucleic acid that pre-exists in the target cell. In many embodiments, the sequence of nucleotides present in the exogenous nucleic acid will be one that is not found in the genome of the target cell. The subject methods can be used with a variety of target cells. Target cells with which the subject vectors may be employed are generally animal or plant cells, where in many embodiments the target cells are animal cells. Of particular interest in many embodiments is the use of the subject vectors to target vertebrate cells, particularly avian cells, e.g. chicken cells; mammalian cells, including murine, porcine, ovine, equine, rat, dog, cat, monkey, and human cells; and the like.

In the methods of the subject invention, a P element derived vector as described above is introduced into a target cell under conditions sufficient for excision of the P feet flanked nucleic acid from the vector and subsequent integration of the excised nucleic acid into the genome of the target cell. As the P element derived vector is introduced into the cell "under conditions sufficient for excision and integration to occur," the subject method further includes a step of ensuring that the requisite transposase activity is present in the target cell along with the introduced vector. Depending on the structure of the vector itself, i.e. whether or not the vector includes a region encoding a product having P element transposase activity, the method may further include introducing a second vector into the target cell which encodes the requisite transposase activity.

The vector (and second vector where necessary) may be introduced into the target cell using any convenient protocol, where the protocol may provide for in vitro or in vivo introduction of the vector. A number of different in vitro protocols exist for introducing nucleic acids into cells, and may be employed in the subject methods. Suitable protocols include: calcium phosphate mediated transfection; DEAE-dextran mediated transfection; polybrene mediated transfection; protoplast fusion, in which protoplasts harboring amplified amounts of vector are fused with the target cell; electroporation, in which a brief high voltage electric pulse is applied to the target cell to render the cell membrane of the target cell permeable to the vector; liposome mediated delivery, in which liposomes harboring the vector are fused with the target cell; microinjection, in which the vector is injected directly into the cell, as described in Capechhi et al, Cell (1980) 22: 479; and the like. The above in vitro protocols are well known in the art and are reviewed in greater detail in Sambrook, Fritsch & Maniatis, Molecular Cloning: A Laboratory Manual (Cold Spring Harbor Laboratory Press)(1989) pp16.30–16.55. In vivo protocols that find use in delivery of the subject vectors include delivery via lipid based, e.g. liposome vehicles, where the lipid based vehicle may be targeted to a specific cell type for cell or tissue specific delivery of the vector. Patents disclosing such methods include: U.S. Pat. Nos. 5,877,302; 5,840,710; 5,830,430; and 5,827,703, the disclosures of which are herein incorporated by reference. Other in vivo delivery systems may also be employed, including: the use of polylysine based peptides as carriers, which may or may not be modified with targeting moieties, microinjection, electroporation, and the like. (Brooks, A. I., et al. 1998, J. neurosci. Methods V. 80 p: 137–47; Muramatsu, T., Nakamura, A., and H. M. Park 1998, Int. J. Mol. Med. V. 1 p: 55–62)

The amount of vector nucleic acid that is introduced into the cell is sufficient to provide for the desired excision and insertion of the exogenous nucleic acid into the target cell genome. As such, the amount of vector nucleic acid introduced should provide for a sufficient amount of transposase activity and a sufficient copy number of the exogenous nucleic acid. The amount of vector nucleic acid that is introduced into the target cell varies depending on the efficiency of the particular introduction or transfection protocol that is employed.

Following introduction of the vector DNA into the target cell in combination with the requisite transposase, the nucleic acid region of the vector that is flanked by the P feet of the vector, i.e. the vector nucleic acid positioned between the P element transposase recognized 31 base pair terminal repeats, is excised from the vector via the provided transposase and inserted into the genome of the targeted cell. As such, introduction of the vector DNA into the target cell is followed by subsequent transposase mediated excision and insertion of the exogenous nucleic acid carried by the vector into the genome of the targeted cell.

Because of the particular properties of the subject transposon based vectors, the subject vectors may be used to integrate large pieces of DNA into a target cell genome. Generally, the size of DNA that the vectors insert into a target cell genome is at least about 50 bp, usually at least about 1000 bp and more usually at least about 2000 bp, where the size may be as large as 150,000 bp or larger, but generally does not exceed about 20,000 bp and usually does not exceed about 10,000 bp. Where the vector inserts a large piece of DNA into a target cell genome, the size of the inserted DNA ranges from about 30 to 150 kb.

The subject methods of stable integration of exogenous nucleic acid into the genome of a target cell find use in a variety of applications in which the stable integration of an exogenous nucleic acid into a target cell genome is desired. Applications in which the subject vectors and methods find use include: research applications, polypeptide synthesis applications and therapeutic applications. Each of these representative categories of applications is described separately below in greater detail.

Research Applications

Examples of research applications in which the subject vectors find use include applications designed to characterize a particular gene. In such applications, the vector is employed to insert a gene of interest into a target cell and the resultant effect of the inserted gene on the cell's phenotype is observed. In this manner, information about the gene's activity and the nature of the product encoded thereby can be deduced. The vectors can also be employed to identify and define DNA sequences that control gene expression, e.g. in a temporal (e.g. certain developmental stage) or spatial (e.g. particular cell or tissue type) manner. In such assays, the subject vectors are employed to stably integrate into the genome of a target cell a selectable marker gene, e.g. antibiotic resistance, LacZ, etc., where the vector lacks a sufficient promoter for the marker the gene such that the marker is not significantly expressed, if at all, unless it is underneath an endogenous promoter element. If the marker gene is inserted into the target cell genome in sufficient relationship to an endogenous promoter sequence, it will be expressed. From the resultant expression profile of the marker gene, the endogenous promoter that is mediating its expression can then be characterized. Yet another research application in which the subject vectors find use is in the identification and characterization of the results of gene expression studies. For example, a plurality of distinct vector targeted cells (or animals produced therefrom) are prepared in which the gene of interest is inserted into distinct locations in the genome of various targeted cells, where expression of the gene of interest is dependent on endogenous promoter mediation, i.e. where the gene of interest lacks a promoter or is coupled to only a weak promoter. By plurality is meant at least two, where the number usually ranges from about 2 to 5000, usually from about 2 to 200. This plurality of vector targeted cells may be produced by introducing the vector in a plurality of cells or taking a collection of pretargeted cells that are homogenous with respect to the insertion site of the gene, i.e. progeny of a single targeted cell, and then introducing transposase into one or more of, but not all of, the constituent members of the collection. The subject vectors can also be used to study integration mutants, where a gene of interest is inserted randomly into the genome and the affects of this random insertion of the targeted cell phenotype are observed. One can also employ the subject vectors to produce models in which overexpression and/or misexpression of a gene of interest is produced in a cell and the effects of this mutant expression pattern are observed. One can also use the subject vectors to readily clone genes introduced into a host cell via insertional mutagenesis that yields phenotypes and/or expression patterns of interest. In such applications, the subject vectors are employed to generate insertional mutants through random integration of DNA. The phenotype and/or expression pattern of the resultant mutant is then assayed using any convenient protocol. In those mutants of interest, cloning of the DNA associated with the phenotype and/or expression pattern of interest is readily accomplished through use of the P-feet of the subject vector.

Polypeptide Synthesis Applications

In addition to the above research applications, the subject vectors also find use in the synthesis of polypeptides, e.g. proteins of interest. In such applications, a vector that includes a gene encoding the polypeptide of interest in combination with requisite and/or desired expression regulatory sequences, e.g. promoters, etc., (i.e. an expression module) is introduced into the target cell that is to serve as an expression host for expression of the polypeptide. Following introduction and subsequent stable integration into the target cell genome, the targeted host cell is then maintained under conditions sufficient for expression of the integrated gene. Once the transformed host expressing the protein is prepared, the protein is then purified to produce the desired protein comprising composition. Any convenient protein purification procedures may be employed, where suitable protein purification methodologies are described in Guide to Protein Purification, (Deuthser ed.) (Academic Press, 1990). For example, a lysate may be prepared from the expression host expressing the protein, and purified using HPLC, exclusion chromatography, gel electrophoresis, affinity chromatography, and the like.

Therapeutic Applications

The subject vectors also find use in therapeutic applications, in which the vectors are employed to stably integrate a therapeutic nucleic acid, e.g. gene, into the genome of a target cell, i.e. gene therapy applications. The subject vectors may be used to deliver a wide variety of therapeutic nucleic acids. Therapeutic nucleic acids of interest include genes that replace defective genes in the target host cell, such as those responsible for genetic defect based diseased conditions; genes which have therapeutic utility in the treatment of cancer; and the like. Specific therapeutic genes for use in the treatment of genetic defect based disease conditions include genes encoding the following products: factor VIII, factor IX, β-globin, low-density protein receptor, adenosine deaminase, purine nucleoside phosphorylase, sphingomyelinase, glucocerebrosidase, cystic fibrosis transmembrane regulator, α-antitrypsin, CD-18, ornithine transcarbamylase, arginosuccinate synthetase, phenylalanine hydroxylase, branched-chain α-ketoacid dehydrogenase, fumarylacetoacetate hydrolase, glucose 6-phosphatase, α-L-fucosidase, β-glucuronidase, α-L-iduronidase, galactose 1-phosphate uridyltransferase, and the like. Cancer therapeutic genes that may be delivered via the subject vectors include: genes that enhance the antitumor activity of lymphocytes, genes whose expression product enhances the immunogenicity of tumor cells, tumor suppressor genes, toxin genes, suicide genes, multiple-drug resistance genes, antisense sequences, and the like. Because of the length of nucleic acid that can be carried by the subject vectors, the subject vectors can be used to not only introduce a therapeutic gene of interest, but also any expression regulatory elements, such as promoters, and the like, which may be desired so as to obtain the desired temporal and spatial expression of the therapeutic gene.

The following examples are offered by way of illustration and not by way of limitation.

EXPERIMENTAL

I. Preparation of a P Element Derived Vector

Figure 2:
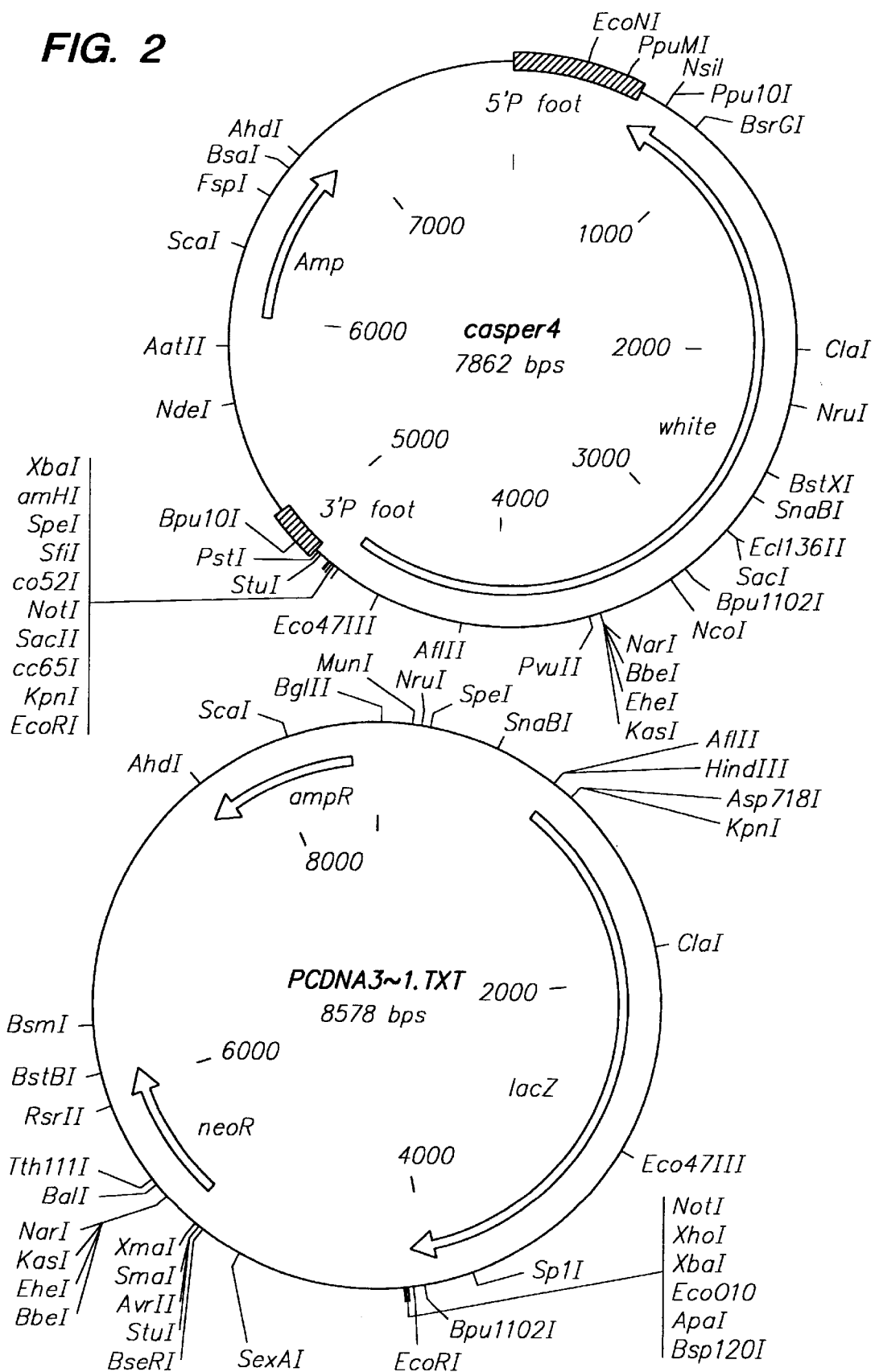
FIG. 2 provides a diagram showing the synthesis of the vector depicted in FIG. 1.

The Gene Transfer Vector depicted in FIG. 1 was prepared by digesting the pcdna3.1hislacz vector shown in FIG. 2 with the restriction endonucleases BglII and BstBI. This gave rise to a 6 kb fragment and a 2.5 kb fragment of DNA. The 6.5 kb fragment contained the neo and lacz genes and was used to construct the gene transfer vector. pCasper4 (depicted in FIG. 2) was treated with restriction endonucleases ClaI and BamHI. This gave rise to a 2.8 kb and a 5 kb fragment of DNA. The 5 kb fragment that contained the P element inverted repeats, which are required for P element mobilization and integration, was used to construct the gene transfer vector. The 5 kb ClaI, BamHI fragment of DNA from pCasper4 was ligated to the 6 kb BglII, BstBI fragment of DNA from pcdna3.1hislacz. This formed the new vector as diagramed below. Variants of this vector have been made that continue to function. Variants that have been made include replacing the lacz gene with the gfp gene and adding a multiple cloning polylinker.

II. Transfection of Cells with a P Element Derived Vector

The ability of the vector produced in I above to transfect a number of different types of cells was tested.

A. QT6 Fibroblast Cells

A P element derived vector as produced in 1 above was transiently transfected into cultured QT6 fibroblast cells. A separate vector, pTURBO (W. R. Engels, Bioess. 14: 681–686 (1992) that contained the P element transposase gene was also transfected into these cells. The integration of the P element transposon domain of the vector (i.e. that domain of the vector flanked by the P feet) was determined by long term growth (13 days) on medium containing 200 $\mu$g/ml of G418, a neomycin like antibiotic. The G418 resistant cells were all betagalactosidase positive (not shown). G418 resistance was dependent on both the P element based vector and the P transposase vector being co-transfected into the QT6 cells. Either vector alone yielded no G418 resistant cells. In addition, the number of G418 resistant cells is concentration dependent upon the amount of DNA introduced into the cell. The results are provided in Table 1, infra. When 1 $\mu$g of the P element w/lacZ and G418r genes was transfected into QT6 cells alone, lacz gene expression was no longer detected in cells not under G418 treatment after 10 days (not shown). Transfections were carried out using standard calcium chloride protocols.

TABLE 1

The P element based vector containing the G418r gene confers stable resistance only when introduced into QT6 cells along with the transposase producing vector.

| DNA transfected into cells ($\mu$g) | | % of cells surviving 13 days |
|---|---|---|
| Transposase producing vector | P element based vector w/lacZ + G418$^r$ | under 200 $\mu$g/ml of G418 selection* |
| 0 | 0 | 0 |
| 0 | 1 | 0 |
| 3 | 0 | 0 |
| .1 | .5 | 1–5% |
| .5 | .5 | 20% |
| 3 | .5 | 50% |
| .5 | .5 | 20% |
| .5 | 2 | 25% |
| .5 | 5 | 50% |

*Percentage is determined by the number of cells that survive/total number of original cells, taking into account doubling time.

QT6 cells transfected with transposase and P element maintain the gene expression for both the lacZ and G418r for at least 30 days.

The above results indicate that the P element based transposon vector integrates into the genome in a transposase dependent manner.

To determine the vector attributes necessary for transformation of QT6 cells, as described above, various control vectors were assembled according to the methods described above and the ability of these controls to transfect QT6 cells was determined.

The results are provided in Table 2.

TABLE 2

| DNA transfected into cells ($\mu$g) | | | % of cells surviving 13 days |
|---|---|---|---|
| Transposase producing vector | P element based vector w/G418$^r$ only | P element based vector w/G418$^r$ + Bluescript DNA* | under 200 $\mu$g/ml of G418 selection* |
| .1 | .5 | — | 0 |
| .5 | .5 | — | 0 |
| 3 | .5 | — | 0 |
| 3 | 1 | — | 0 |
| .5 | 2 | — | 0 |
| .5 | 5 | — | 0 |
| .1 | — | .5 | 0 |
| .5 | — | .5 | 0 |
| 3 | — | .5 | 0 |
| 3 | — | 1 | 0 |
| .5 | — | 2 | 0 |
| .5 | — | 5 | 0 |

*Percentage is determined by the number of cells that survive/total number of original cells, taking into account doubling time.

The above results indicate that successful integration and gene expression is dependent upon having two transcriptionally active genes. One gene alone (G418$^r$) does not enable integration. In addition, the size of the vector is not an important requirement as a transcriptionally inert DNA was substituted in place of the lacZ gene, which kept the overall size of the construct constant.

B. Mouse Embryonic Stem Cells (CCE)

The vector prepared in I above was used to integrate the kanamycin and betagalactosidase genes into mouse embryonic stem cells in a method analogous to that described in IIA above. The results are provided in Table 3.

TABLE 3

| DNA transfected into cells ($\mu$g) | | % of cells surviving 20 days |
|---|---|---|
| Transposase producing vector | P element based vector w/G418$^r$ and LacZ | under 200 $\mu$g/ml of G418 selection* |
| 0 | 0 | 0 |
| 1 | 0 | 0 |
| 0 | 1 | 0 |
| 1 | 1 | 50% |

D. Human Kidney Cells (293)

The vector prepared in I above was used to integrate the kanamycin and betagalactosidase genes into human kidney cells in a method analogous to that described in IIA above. The results are provided in Table 4.

TABLE 4

| DNA transfected into cells (µg) | | % of cells surviving 13 days under 400 µg/ml of G418 selection* |
|---|---|---|
| Transposase producing vector | P element based vector w/G418$^r$ and LacZ | |
| 0 | 0 | 1% |
| 1 | 0 | 1% |
| 0 | 1 | 5% |
| 1 | 1 | 70% |

It was difficult to find an antibiotic treatment which would kill all cells that were being analyzed.

The above results demonstrate that the subject P element based vectors are capable of stably integrating exogenous nucleic acids into the genome of vertebrate cells, and in particular mammalian cells. As such, the above results demonstrate that the subject vectors are suitable for use as vectors for use in the introduction of exogenous nucleic acids into mammalian cells.

E. Integration of a Large DNA Fragments into a Target Cell

P element vectors have the capability to mobilize up to 150 kb of DNA. This presents the opportunity of the P element carrying a DNA sequence with therapeutic use of similar length into a target cell. The manipulation and handling of DNA fragments up to 4 megabases is difficult but has been reproducibly achieved. For example, this vector could allow the potential for analyzing genes on the size of the human huntington gene (~150–200 kb).

III. Gene Therapy

Once the gene transfer vector has been engineered with the desired gene and its regulatory sequences according to the methods described above, the construct must reach the receipient cell's nucleus to achieve gene integration. Many methods exist to achieve the transfer of this vector into a recipient cell. For instance microinjection into mouse oocyte/embryo nuclei would be optimal for creating a germ line transfer of genetic material. This could also be achieved by transfecting mouse embryonic stem cells, selecting the cells that have had the desired genetic material transferred into the genome and then implanting these cells into pseudo-pregnant females.

Several methods have been shown to transfer genetic material into human cells. Direct injection of naked DNA has been shown to be taken up and expressed transiently in muscle cells. While other methods use lipid or protein conjugates to facilitate the uptake of DNA. Finally, electric current has also been shown to achieve transfer of DNA in organisms.

VI. Gene Therapy in Mice

A 6 week old male mouse (30 grams in weight) was injected with 5 micrograms of the integration vector and 2 micrograms of the transposase containing vector. The standard procedure from mirus transit in vivo gene delivery system was used for the injection. Briefly, this procedure combines the DNA to a lipid carrier to help protect the DNA from degradation in the blood and to assist the DNA to be uptaken by cells in the animal. The injection was into the tail vein of the animal. At 15 weeks of age, tissue samples were taken from the liver, testis, and tail. Genomic DNA was isolated from these samples using the standard proteinase k/spooling technique. These preparations of genomic DNAs were subjected to PCR analyses.

The presence of the integration vector was examined using primers to the beta-galactosidase gene while the presence of the transposase containing vector was examined using primers to the transposase gene. Genomic DNA from the tail of the untreated control mouse showed an absence of both the beta-galactosidase and transposase genes. This control was not surprising as neither the transposase nor beta-galactosidase genes are endogenous to the mouse genome. However, 9 weeks after the integration and transposase vectors were injected into the test mouse, the beta-galactosidase gene was easily detectable. This indicated that the integration vector had inserted into the genomic DNA in all the tissues examined. The absence of the transposase vector in the genomic DNA indicates that DNA did not randomly integrate into the mouse genome and that the integration vector did so via its standard mechanism. To ensure that both sets of PCR primers were capable of amplifying a low concentration of target DNA, both the transposase and beta-galactosidase genes are detectable from mixing 0.01 nanograms of integration vector and transposase vector DNAs into the genomic DNA of the untreated mouse.

TABLE 1

Gene integration in mice

| DNA | | PCR results from betagalactosidase gene | PCR results from transposase gene |
|---|---|---|---|
| Untreated mouse | Tail genomic | – | – |
| Vector treated mouse | Tail genomic | + | – |
| | Liver genomic | + | – |
| | Testis genomic | + | – |
| Untreated mouse | Tail genomic + .01 ng of betagalactosidase vector | + | – |
| Untreated mouse | Tail genomic + .01 ng of transposase vector | – | + |

This data indicates that this vector can be used for somatic cell gene therapy. Furthermore, the integration into testis cells also indicates that the subject vector finds use in germ line applications.

It is evident from the above results and discussion that the subject invention provides a novel nucleic acid vector having a broad range of applications. Advantages of the subject vector over other known nucleic acid vectors include the ability to integrate long stretches of nucleic acid into the genome of a target cell. This feature is advantageous for a number of reasons, including the ability to integrate an exogenous gene along with its native expression regulatory elements. Another feature of the subject invention is that the vectors provide for random insertion of a foreign nucleic acid, which is desirable in many applications. Yet another advantage of the subject invention is that the subject vectors do not elicit host immune reactions, in contrast with many viral based vectors. In addition, the subject vectors do not carry risk of viral infection or recombination hazards. As such, the subject vectors provide a number of advantages over other vectors currently known and employed in the art, and therefore represent a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A P element vector for introducing an exogenous nucleic acid into a target non-insect cell genome, said vector comprising: a pair of P element transposase recognized insertion sequences flanking at least two non-insect cell transcriptionally active expression modules each comprising a coding sequence and a promoter.

2. The vector according to claim 1, wherein said vector further comprises at least one endonuclease cleavage site.

3. The vector according to claim 1, wherein said endonuclease cleavage site is present in a polylinker.

4. The vector according to claim 1, wherein said vector further comprises transposase domain encoding a product having P element transposase activity, wherein said transposase domain is not flanked by said pair of transposase recognized insertion sequences.

5. The vector according to claim 1, wherein said vector further comprises an exogenous sequence positioned at a site between said pair of transposase recognized insertion sequences.

6. The vector according to claim 1, wherein said transposase recognized insertion sequences are 31 base pair inverted repeats.

7. A P element vector for introducing an exogenous nucleic acid into a non-insect target cell genome, said vector comprising: a pair of P element derived 31 base pair inverted repeats flanking at least two non-insect cell transcriptionally active genes, wherein each of said transcriptionally active-expression modules each comprising a coding sequence that is expressed under intracellular conditions.

8. The vector according to claim 7, wherein said vector further comprises a nucleic acid sequence encoding a product having P element transposase activity positioned external to the vector domain flanked by said pair of P element derived 31 base pair inverted repeats.

9. The vector according to claim 7, wherein said vector further comprises an exogenous nucleic acid positioned between said P element derived 31 base pair inverted repeats.

10. A method of inserting an exogenous nucleic acid into a non-insect target cell genome, said method comprising:
introducing into said cell a P-element derived vector comprising said exogenous nucleic acid under conditions sufficient for transposition to occur;
whereby said exogenous nucleic acid is inserted into said genome; with the proviso that said target cell is not an insect cell.

11. The method according to claim 10, wherein said target cell is an animal or plant cell.

12. A method of inserting an exogenous nucleic acid into a non-insect target cell genome, said method comprising:
introducing into said cell a vector according to claim 1 under conditions sufficient for transposition to occur;
whereby said exogenous nucleic acid is inserted into said genome.

13. The method according to claim 12, wherein said vector comprises a transposase domain.

14. The method according to claim 12, wherein said method further comprises introducing a second vector comprising a transposase domain into said cell.

15. The method according to claim 12, wherein said exogenous nucleic acid ranges in length from about 50 to 150,000 bp.

16. The method according to claim 12, wherein said target cell is a vertebrate cell.

17. The method according to claim 16, wherein said vertebrate cell is a mammalian cell.

18. A kit for use in inserting an exogenous nucleic acid into a non-insect target cell, said kit comprising:
a P element vector comprising a pair of P element transposase recognized insertion sequences flanking at least two non-insect cell transcriptionally active expression modules each comprising a coding sequence and a promoter.

19. The kit according to claim 18, wherein said vector further comprises at least one endonuclease cleavage site positioned between said transposase recognized insertion sequences.

20. The kit according to claim 19, wherein said endonuclease cleavage site is present in a polylinker.

21. The kit according to claim 18, wherein said kit further comprises a nucleic acid sequence encoding a product having P element transposase activity.

22. The kit according to claim 21, wherein said vector comprises said nucleic acid sequence encoding a product having transposase activity.

23. The kit according to claim 21, wherein said nucleic acid sequence encoding a product having transposase activity is present on a second vector.

24. The kit according to claim 18, wherein said transposase recognized insertion sequences are 31 base pair inverted repeats.

* * * * *